(12) United States Patent
Ching et al.

(10) Patent No.: US 6,753,413 B1
(45) Date of Patent: Jun. 22, 2004

(54) P35$^{NCK5A}$ BINDING PROTEINS

(75) Inventors: Yick Pang Ching, Sai Kung (HK); Jerry H. C. Wang, Hong Kong (HK)

(73) Assignee: The Hong Kong University of Science & Technology, Hong Kong (CN)

( * ) Notice: Subject to any disclaimer, the term of this patent is extended or adjusted under 35 U.S.C. 154(b) by 44 days.

(21) Appl. No.: 09/652,603

(22) Filed: Aug. 30, 2000

Related U.S. Application Data

(60) Provisional application No. 60/151,584, filed on Aug. 30, 1999.

(51) Int. Cl.$^7$ .............................................. C07K 17/00
(52) U.S. Cl. ...................................................... 530/352
(58) Field of Search ................................ 530/350, 352

(56) References Cited

PUBLICATIONS

Ngo et al., in The Protein Folding Problem and Tertiary Structure Prediction, 1994, Merz, et al., (ed.), Birkhauser, Boston, MA, pp. 433 and 492–495.*

Skolnick et al., From genes to protein structure and function: novel applications of computational approaches in the genomic era, Jan. 2000, Trends in Biotech. 18(1): 34–39.*

Attwood et al., The babel of bioinformatics, Oct. 2000, Science 290 (5491): 471–473.*

Mikayama et al, Molecular cloning and functional expression of a cDNA encoding gycosylation–inhibting factor, Nov. 1993, Proc. Natl. Acad. Sci, USA vol. 90: 10056–10060.*

Wang, Xiujie et al; "Identification of a Common Protein Association Region in the Neuronal Cdk5 Activator", *The Journal of Biological Chemistry*, vol. 275, No. 41, Issue of Oct. 13, pp 31763–31769, 2000, USA.

Ching, Qi, & Wang, "Cloning of three novel neuronal Cdk5 activator binding proteins", *GENE*, Gene 242 (2000) 285–294, USA.

Qi, Tang, Zhu, Fujita & Wang, "Association of Neurofilament Proteins with Neuronal Cdk5 Activator", The Journal of Biological Chemistry, pp 2329–2335, vol. 273, No. 4, Issue of Jan. 23, 1998, USA.

\* cited by examiner

*Primary Examiner*—Christina Chan
*Assistant Examiner*—Phuong N. Huynh
(74) *Attorney, Agent, or Firm*—Dority & Manning, PA

(57) ABSTRACT

The present invention concerns novel proteins capable of binding p35$^{nck5a}$, and method of use of same.

6 Claims, 6 Drawing Sheets

(3 of 6 Drawing Sheet(s) Filed in Color)

Figure 1
A)
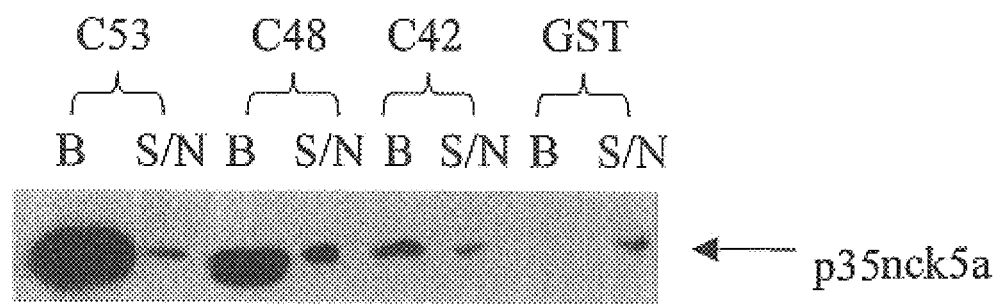
B)
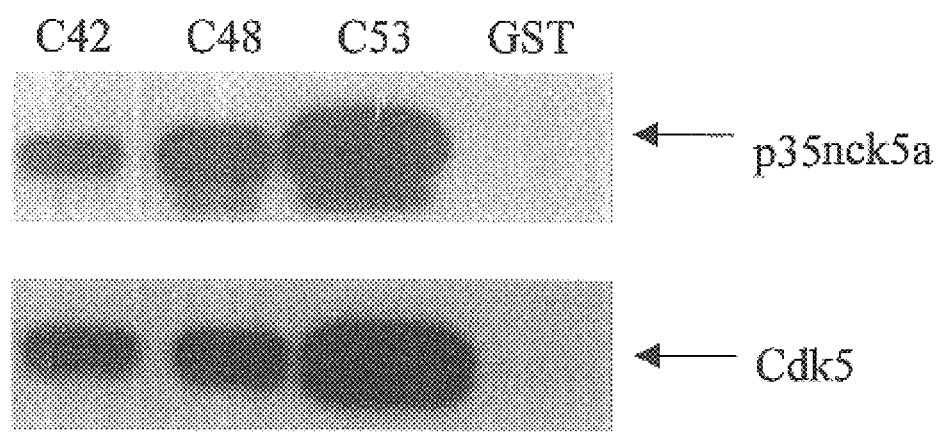

```
A. thaliana    MASSSLSSLSSILSNPHGCSLCFKASTQRCFALRFLSSKATHASSSSSSALLPRCRSSTH  60
C42            ----------------------MHPLQRVFRAQRLSAPLT--S--MCWVLLRTFR--AH  31
C. elegans     -------------------------MLRQWWLRSVGSCST------------VYR--AH  20
                                        *  :   : :.:  *                  *  :*

A. thaliana    RLTQKPINRKKGFSLNLSRSFSISQIASSGKFDGPSLHQFVSNAQAHAS--LTTPETESD 118
C42            NSTSCPDPEGK-SSEGVQKDFS-SRLAT-----GPTFQHFLRSASVPQEK-PSSPEVE-- 81
C. elegans     SGCSTSAAVKP------KRAIP---TD------GLQLSDFIKESTKKQRQKAIIPSIE-- 63
                 .   .        .: :.           *   :.*: .:         *. *

A. thaliana    SIFYKRLLSNCGLCCIAYIDANTFLFGFILALRSTLDSDIASKGRIYHETYGCQMNINDM 178
C42            -------------------DPPPYLSG---------DELLGRQRKVYLETYGCQMNVNDT 113
C. elegans     -------------------DTKEYLNP---------EDLQGNGRTVCYVTYGCQMNVSDM 95
                                    *.  :*           :.  .    : *******:.*

A. thaliana    EIVLAIMKNSGYKEVVTDPESAEVIFVNTCAIRENAEQRVWQRLNYFWFLKREWKVNAAT 238
C42            EIAWSILQKSGYLR-TSNLQEADVILLVTCSIREKAEQTIWNRLHQLKVLK---AK---- 165
C. elegans     EIVRSIMTKYGFVE-SDKKENADIVLLMTCSIRDGAEKKVWN---QLKLIR---SN---- 144
               **.:*: : *:  . .:.*:::: **:**: **:  :*:     : .::

A. thaliana    GRAKSLKPPKVVVLGCMAERLKDKILDSDKMVDVVCGPDAYRDLPRLLEEVDYGQKGINT 298
C42            -RPRSRVPLRIGILGCMAERLKGEILNREKMVDLLAGPDAYRDLPRLLAVVESGQQAANV 224
C. elegans     ---SVNKGQIVGVLGCMAERVRHDLLEKRNLVNIVAGPDSYRDLPRLVAVAAGGSNGINV 201
                    : :******:: ..*:  ::*:::.***:*******:  .*. .*.

A. thaliana    LLSLEETYADISPVRISENSITAFVSVMRGCNNMCAFCIVPFTRGRERSRPVESIIREVG 358
C42            LLSLDETYADIMPVQTSPSATSAFVSIMRGCDNMCSYCIVPFTRGRERSRPVASILDEVR 284
C. elegans     QLSLDETYADVQPIRVDSASKTAFISIMRGCDNMCTYCVVPFTRGRERSRPIESIVEEVQ 261
                ***:*****: *::    : :**:*:****:***  *:************: ** **

A. thaliana    ELWESGVKEVTLLGQNVNSYNDDS-ADR---ESGANWEYSEGFSSRCKVKNMGLRFADLL 414
C42            NVSEQGLKEVTLLGQNVNSFRDNSEVQF---SSTGSANLSRGFTTNYKPKQGGLRFSHLL 341
C. elegans     RLRDQGYKQVTLLGQNVNSYRDMTSMDFSMAPSTSQEDRVPGFKTVYKPKSGGLTFTTLL 321
                . :.* *:**********:.*  :  *   :   *  .: **  .:  *  ** * **

A. thaliana    DRLSVEFPEMRFRFTSPHPKDYPDELLYLMRDRHNICNLIHLPAQSGNSRILEQMRRGYT 474
C42            DQVSRIDPEMRIRFTSPHPKDFPDEVLQLIRERHNICKQIHLPAQSGSSRVLEAMRRGYS 401
C. elegans     EKVADAAPDIRFRFTSPHPKDFPMQLIELIASRPNLCKQLHLPAQSGDDETLERMERGYT 381
                ::::    *: :**********:*  *::*::    * :* :*******... ** *.***.

A. thaliana    REAYLDLVKKIRSIIPDVAITSDFITGFCGETEEEHQETLSLVRAVGYDMAYMFAYSMRE 534
C42            REAYVALVHHIREAIPGVGLSSDFITGFCGETEDDHLQTVSLLREVQYNTGFLFAYSMRQ 461
C. elegans     RDLYLRLVDDIRHVLPSVSLTSDFIAGFCGETEQAHQNTLSLIRAVRYSFCFVFPYSMRG 441
               *: *: **..**  :*.*   ****:*******  *:  **::** *.     . :*.***

A. thaliana    KTHAHRNYTDDVPEEVKQRRLTELIDAFRETTGPCYDSQVGSTQLVLVEGPNKRAPETEL 594
C42            KTRAYHRLKDDVPEEVKLRRLEELITVFREEASKVNATSVGCTQLVLVEGFSKRS-TTDL 520
C. elegans     KTRAHHRLTDDVPEDVKARRHLDLTTVFREEALKLNQALIGSEQTVLLEGKSKRD-ASFS 500
               **:*::: .*****:** **  :*  .***:::     .  *  :*:***  *.   :

A. thaliana    IGKTDKGHRVSFVTKPLFDKACLLD-GDDLKRNPGIGDFVEVQIEKSTRASLFGEALAIS 653
C42            CGRNDANLKVIFPDAEVED---ITDPGLKVRAQP--GDYVLVKIISASSQTLKGHILCRT 575
C. elegans     HGRIDGGVKAVFDNS-------------KLCLEP--GQYAKILITDANSQTLKAQLIGQS 545
                *: *  : .*  ..                 *    *:   :: :.**** .: :

A. thaliana    KMSLFHDVGVVDAVVASCAS 673
C42            TMK--------DSSMN-CLT 586
C. elegans     SI------------------ 547
                .:
```

Figure 4

```
Restin  WCGVELDEPLGKNDGAVAGTRYFQCQPKYGLFAPVHKVTKIGFPSTTPAKAKANAVRRVM 300
c48     ---------------------------------------------------------M 1
                                                                   *

Restin  ATT SASLKRSPSASSLSSMSSVASSVSSRPS RTGLLTETSSRYARKISGTTALQEALKEK 360
c48     APK SASETPVLSGTDVDSLSCDSTSSATSPS CMPCLVAGRHLWASKSG------------ 49
        *..***  . *..:..*:*. ::*  :: ** *.       :* *  .

Restin  QQHIEQLLAERDLERAEVAKATSHVGEIEQELALARDGHDQHVLELEAKMDQLRTMVEAA 420
c48     -HHMLCLIEDYDALYKQISWGQTLLAKMDIQTQEALSPTSQKLGPKASFSVPLSKFLSSM 108
         :*:   *: : *    :::  . : :..::: :   *  . .*::     :   * .::..:

Restin  DREKVELLNQLEEEKRKVEDLQFRVEEESITKGDLETQTKLEHARIKELEQSLLFEKTKA 480
c48     N--TAKLI--LEKASR-LLKLFWRVSVP--TNG----QCSLHCDQIGEMKAEITKLHKKL 157
        :  ..:*:  **: .* : .*  :**.    *:*    * .*.  :* *:: .:   :.*

Restin  DKLQRELEDTRVATVSEKSRIMELEKDLALRVQEVAELRRRLESNKPAGDVDMSLSLLQE 540
c48     FEQEKKLQNTAKLLQQSKHQEKIIFDQLVITHQVLRKARGNLEL-RPRAAHPGTSSPSRP 216
         : :::*::*      ..*  :    : ..*.:  *  :  *  .**  :*  .   : *   :

Restin  ISSLQEKLEVTRTDHQREITSLKEHFGAREETHQKEIKALYTATEKLSKENESLKSKLEH 600
c48     G----------------------------------------------------------- 217
```

P35^NCK5A BINDING PROTEINS

RELATED APPLICATIONS

This application claims the benefit of U.S. Provisional Application No. 60/151,584 filed on Aug. 30, 1999.

FIELD OF THE INVENTION

The present invention concerns novel proteins capable of binding $p35^{nck5a}$, and method of use of same.

BACKGROUND OF THE INVENTION

As discussed in Ching Y P et al. ("Cloning of three novel neuronal Cdk5 activator binding proteins.", Gene. Jan. 25, 2000;242(1–2):285–94; PMID: 10721722), $p35^{nck5a}$ is a 35 kDa neuronal-specific protein from which is derived a 25 kDa activator protein named $p25^{nck5a}$ which, together with a catalytic subunit named Cdk5 (cyclin dependent kinase 5), forms an active kinase named neuronal cdc2-like kinase (Nclk), which is involved in the regulation of neuronal differentiation and neuro-cytoskeleton dynamics (Lew J et al., "Neuronal cdc2-like kinase.", Trends Biochem Sci. January 1995;20(1):33–7; PMID: 7878742). Cdk5 itself exists in three distinct states:

i) a free monomer;

ii) a form in association with $p25^{nck5a}$; and iii) a form complexed with $p35^{nck5a}$ (Lee K Y et al., J Biol Chem. Jan. 19, 1996; 271(3):1538–43; PMID: 8576150).

The free monomeric form can be activated by bacterially expressed $p25^{nck5a}$, whereas the $p25^{nck5a}$-associated Cdk5 possesses endogenous kinase activity, and cannot be further activated. The form complexed with full length $p35^{nck5a}$ demonstrates no enzymatic activity even when exogenously activated, suggesting that the Cdk5 activity is suppressed. Further characterization shows that the $p35^{nck5a}$/Cdk5 complex is a macromolecular complex of over 600 kDa in size. The simplest level of regulation may be revealed by the fact that Cdk5 is present in excess of its activators. Nck5a is thus essentially acting as the limiting factor for Cdk5 activity. However, it is still a mystery with regard to the functional difference between the intact and truncated activators. Therefore, it is very useful to uncover the identities of the various binding proteins in the macromolecular protein complex.

With regard to Cdk5, as well as being able to associate with $p25^{nck5a}$, it can also associate with cyclin D and cyclin E but no kinase activity can be demonstrated. While Nck5a contains a very limited sequence homology to members of the cyclin family, evidence has shown that the structure of $p25^{nck5a}$ acquires a folding similar to that of cyclin. Northern analysis has indicated that Nck5a as well as its isoform, p39, are confined in neuronal tissue. Not only has Cdk5 adapted a distinct activator, but the regulation of the Cdk5 kinase activity is also considerably different from other CDKs. For instance, Cdk5 can be fully activated by association with the activator subunit alone, independent of the phosphorylation by Cdk-activating protein kinase (CAK), which is essential for most CDKs to achieve maximum activation. Furthermore, none of the known Cdk inhibitors has been demonstrated to inhibit Cdk5 kinase activity.

Thus proteins which are associated with Nclk, particularly those which bind to it or its subunits (including $p35^{nck5a}$ and Cdk5) and which may therefore affect (i.e. regulate) its activity are of particular interest and use. It has previously been shown (Qi Z et al., "Association of neurofilament proteins with neuronal Cdk5 activator.", J Biol Chem. Jan. 23, 1998;273(4):2329–35; PMID: 9442078) that neurofilament is one of the p35nck5a associated proteins.

SUMMARY OF THE INVENTION

As discussed above, proteins which are associated with Nclk, particularly those which bind to it or its subunits and which may therefore affect (i.e. regulate) its activity, are of particular interest and use. The present inventors have now succeeded in isolating three novel $p35^{nck5a}$ associated proteins which are $p35^{nck5a}$ binding proteins, useful for a variety of purposes as detailed below, particularly as tools to analyse how $p35^{nck5a}$ interacts with other proteins.

Thus the present invention provides a $p35^{nck5a}$ binding protein comprising essentially the sequence of any one of the group consisting of SEQ ID NOs: 2, 4 and 6.

Also provided is a method to screen a large number of molecules or compounds for their ability to form complexes with the $p35^{nck5a}$ binding protein of the invention.

Also provided is a method of using the $p35^{nck5a}$ binding protein of the invention to purify a molecule or compound which specifically binds the $p35^{nck5a}$ binding protein of the invention.

Also provided is a method of determining the binding interaction of $p35^{nck5a}$ with a molecule or compound.

In particular, molecules or compounds (above) are chosen from the group consisting of peptides, agonists, antagonists, inhibitors, antibodies and pharmaceutical agents.

BRIEF DESCRIPTION OF THE FIGURES

The file of this patent contains at least one drawing executed in color. Copies of this patent with color drawing(s) will be provided by the Patent and Trademark Office upon request and payment of necessary fee.

FIG. 1 shows an affinity binding assay of the p35 binding proteins The binding assay was performed as described below. Forty µg of GST, GST-C42 (SEQ ID NO:2), GST-C48 (SEQ. ID NO 4), and GST-C53 (SEQ ID NO 6) proteins were used to pull down either the bacterially expressed $p35^{nck5a}$ protein (panel A) or the baculovirus expressed $p35^{nck5a}$/Cdk5 protein complex (panel B). For panel A, proteins from the supernatant (S/N) (one tenth of the mixture volume) and beads (B) were analysed;

FIG. 4 shows sequence homology alignment for SEQ ID NO 2 (C42) protein and its homologues. The sequence of SEQ ID NO 2 (C42) and its homologues from C.elegans and

Figure 6:
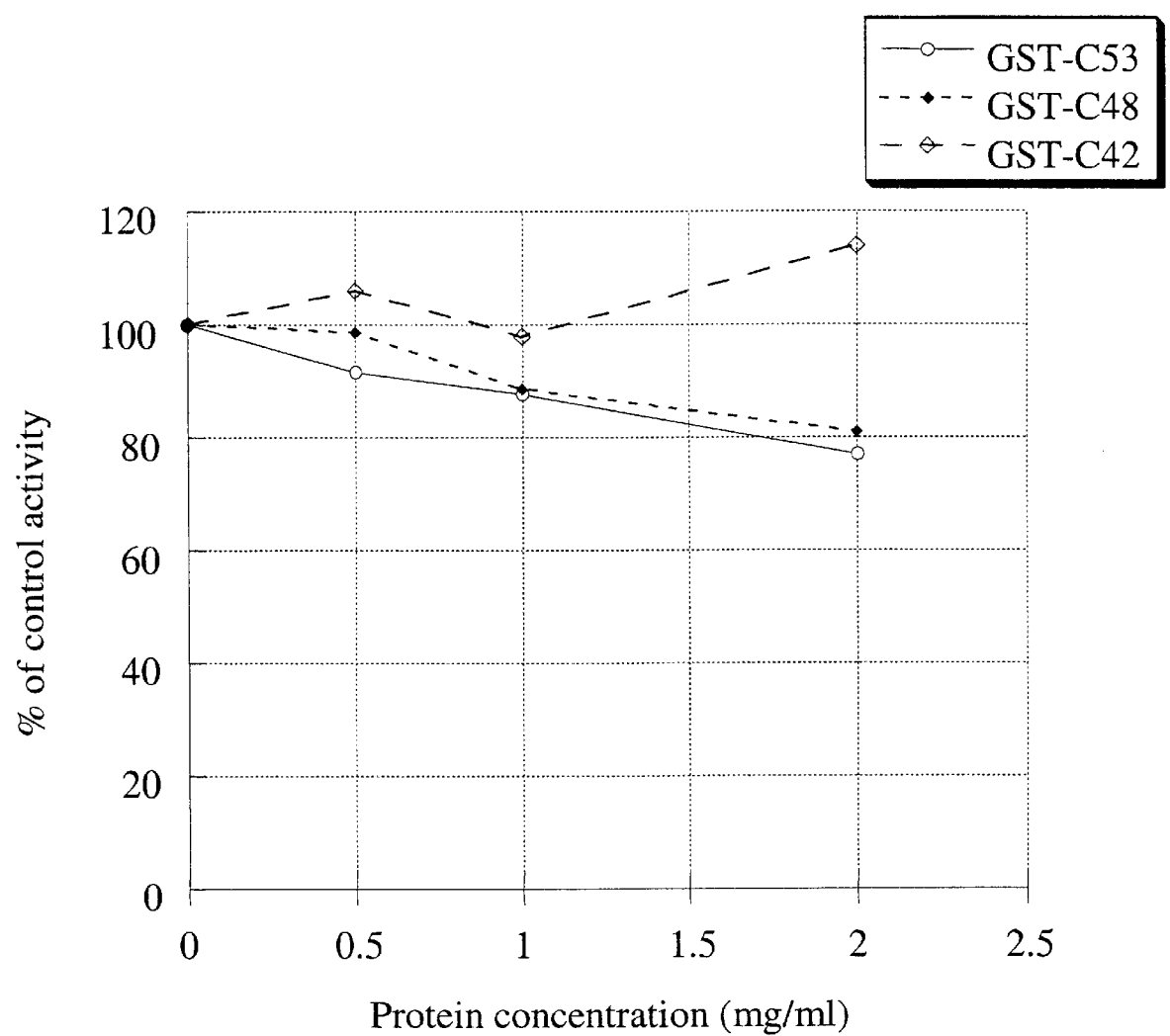

*A.thaliana* were aligned using the multiple sequence alignment program Clustal W (1.74). Amino acids were numbered on the right hand side and the related amino acids are shaded. Identical residues present in all the three proteins are labelled with an asterisk and residue present in only two proteins are labelled with semicolon;

FIG. 5 shows sequence homology alignment for SEQ ID NO. 4 (C48) and restin protein. The alignment of SEQ ID NO 4 (C48) and restin protein was performed by the Clustal W (1.74) program. The corresponding amino acid sequence is numbered on the right hand side and the identical residues are shaped. The serine rich region for both proteins is boxed; and FIG. 6 shows the effect of the binding proteins on Cdk5 kinase activity. GST-Cdk5 (0.6 mg/ml) was reconstituted with GST-p25 (0.3 mg/ml) for 1 hour and assayed for the kinase activity in the presence of indicated amounts of GST-C53 (SEQ ID NO 6) (solid line), GST-C48 (SEQ ID NO 4) (short dotted line) and GST-C42 (SEQ ID NO 2) (long dotted line). Equal amounts of the GST protein was used as a control. X-axis shows protein concentration (mg/ml) from 0–2.5. Y-axis shows % of control activity (0–120%).

DETAILED DESCRIPTION OF THE INVENTION

Using the yeast two-hybrid system to screen for p35-associated proteins has allowed the inventors to identify three clones having novel cDNA sequences. Using these novel cDNA sequences as probes, full length sequence of the novel p35-associated proteins have been isolated from a rat brain cDNA library, and have been shown to interact with p35$^{nck5a}$ in an affinity pulldown assay. A homology search on these full length proteins in sequence databases indicated that SEQ ID NO 4 (C48) may be related to a recently discovered intermediate filament associated protein, called restin (Bilbe G et al., EMBO J. 1992.

The three proteins are called SEQ ID NO 2 (C42), SEQ ID NO 4 (C48) and SEQ ID NO 6 (C53) (NCBI accession numbers AF177477, AF177478 and AF177476 respectively, and have the amino acid sequences of SEQ ID NOs 2, 4 and 6 and the coding sequences of the open reading frames of, respectively, SEQ ID NOs: 1, 3 and 5. They have apparent molecular weights of 66, 24 and 57 kDa respectively.

As well as the specific sequences of SEQ ID NOs: 2, 4 and 6, the invention also extends to variants of the sequences which still display the property of being able to associate (bind) with p35$^{nck5a}$ i.e. the invention is concerned with proteins which comprise essentially the sequences of SEQ ID NOs: 2, 4 and 6. In addition, the proteins of the invention may also have the consensus phosphorylation site for Cdk5, namely a serine or threonine followed by a proline residue. In particular, proteins which comprise essentially the sequences of SEQ ID NOs: 2, 4 and 6 include allelic mutants of the sequences, and sequences having at least 50%, more particularly at least 60, 70, 75, 80, 85, 90, 95, 96, 97, 98 or 99% homology with any of the sequences of SEQ ID NOs: 2, 4 and 6. Examples of allelic mutants are those contained in the rat and human brain libraries used below for library screening and yeast two-hybrid screening. Sequence homology is as determined using the BLAST2 program (Tatusova TA et al., FEMS Microbiol Lett. May 15, 1999; 174(2): 247–50; PMID: 10339815) at the National Center for Biotechnology Information, USA with default parameters. As regards the coding sequences, any variant of the nucleotide sequence may be used so long as it encodes an amino acid sequence of a protein according to the invention. For example, a codon optimised sequence may be used, or other modifications made as desired.

The contents of each of the references discussed herein, including the references cited therein, are herein incorporated by reference in their entirety.

Where "PMID:" reference numbers are given for publications, these are the PubMed identification numbers allocated to them by the US National Library of Medicine, from which full bibliographic information and abstract for the publication is available. This can also provide direct access to electronic copies of the publications, particularly in the case of e.g. PNAS and JBC publications.

Experiments

Materials

Rat brain cDNA libraries were purchased from Stratagene (LaJolla, Calif. 92037) and Clontech Laboratories, Inc (Palo Alto, Calif. 94303-4230). Polyclonal anti-Cdk5 (C-8) and anti-p35 (C-19) antibodies were obtained from Santa Cruz Biotechnology, Inc (Santa Cruz, Calif. 95060). Human Multiple Tissue Northern blotting membrane was from Clontech Laboratories, Inc. All the chemicals were obtained from Sigma (Sigma-Aldrich Corp., St. Louis, Mo. 63031) and Riedel-deHaen, Seelze, Germany.

Isolation of the Full Length cDNA Clones

A total of one million phages were plated out from both rat brain cDNA libraries for the screening of the full length cDNA. The phages DNA were transferred to Hybond nylon membranes according to the protocol suggested by the manufacturer (Amersham, UK). The membranes were pre-hybridized at 42° C. for 2 hours with pre-hybridisation buffer containing 20 mM Pipes, 0.8 mM NaCl, 50% deionised formamide, 0.5% SDS, and 100 µg/ml denatured fragmented salmon sperm DNA. Randomly radiolabelled probes at a specific radioactivity of $10^6$ cpm/ml were then added to fresh pre-hybridisation buffer and the hybridisation was carried out overnight at 42° C. Excess probes were removed by washing the membranes twice in 2×SSC (0.3 M NaCl, 0.03 M trisodium citrate), 0.1% SDS for 10 minutes each at room temperature and once in 0.2×SSC, 0.1% SDS for 10 minutes at 42° C. The membranes were then exposed overnight at −70° C. All the positive clones were isolated after tertiary screening.

Cloning of the full length cDNA into GST fusion protein expression vector: The full length cDNA sequences of SEQ ID NO 6 (C48) and SEQ ID NO 2 (C42) were amplified by polymerase chain reaction (PCR) using the library clones as the template and pfu polymerase as the extension enzyme. For SEQ ID NO 6 (C48), the sense primer is 5'-CGGGATCCAT GGCACCTAAA TCAGCTTC-3' (SEQ ID NO: 7) and the antisense primer is 5'-CGGAATTCTC ATGAGCCCGG TCTGC-3' (SEQ ID NO: 8). For SEQ ID NO 2 (C42), the sense primer is 5'-CCGGATCCAT GCATCCTTTA CAGCGTG-3' (SEQ ID NO: 9) and the antisense primer is 5'-CCGAATTCTC AGGTCAAGCA ATTCATTG-3' (SEQ ID NO: 10). Both amplifications were carried out for 25 cycles at an annealing temperature of 51° C. Purified PCR fragments of expected size were digested with BamHI and EcoRI restriction enzymes, and ligated into the pBluescript II KS(+) vector for double-stranded sequencing. Having confirmed the sequences, the full length cDNA were then subcloned into the pGEX-4T expression vector (Clontech) for protein expression.

The full length SEQ ID NO 6 (C53) expression vector was constructed by direct ligation of the library cDNA insert into the pGEX-4T vector. One library clone contained the full length sequence of SEQ ID NO 6 (C53) with only five more amino acids (GSGKR) (SEQ ID NO: 11) 5' to the first methionine. Thus the whole insert was ligated into the expression vector at the EcoRI cloning site. Restriction mapping and double stranded sequencing further confirmed the exact orientation.

Northern Analysis

Using human multiple tissue Northern blot membrane (Clontech), hybridisation was carried out as suggested by the manufacturer. Northern blot membrane containing approximately 2 µg of poly A+ RNA per lane was pre-hybridised at 68° C. for 1 hour in ExpressHyb (RTM) hybridization solution. Then, hybridisation was performed at 68° C. for 2 hours in ExpressHyb (RTM) hybridization solution plus the specific radiolabelled probe prepared by randomly labelled a SalI/HinfI fragment from SEQ ID NO 2 (C42) (314 bp), a SalI/HindIII fragment from SEQ ID NO (C48) (350 bp) and a SalI/XhoI fragment from SEQ ID NO 6 (C53) (500 bp). The specific activity used for each hybridisation was about $10^6$ cpm/ml.

Expression of Full Length Protein

GST-fusion proteins were purified as described by Tang D et al. (J Biol Chem. May 9, 1997;272(19):12318–27; PMID: 9139676). The expression host used herein was E. coli strain BL21 unless stated otherwise. Bacteria transformed with the DNA constructs were grown to an $A_{600}$ of 1.2 and then induced with 0.2 mM of isopropyl-β-D-thiogalactopyranoside at room temperature for 8 to 12 hours. Cells were harvested by centrifugation and resuspended in MTPBS (150 mM NaCl, 16 mM $Na_2HPO_4$, 4 mM $NaH_2PO_4$) containing 2 mM DTT, 1 µg/ml antipain, 1 µg/ml leupeptin and 1 mM phenylmethylsulfonyl fluoride (PMSF). A French press was used (3 times at 1100 psi) to disrupt the cells and the cell debris was pelleted by centrifugation at 40,000×g for 20 minutes at 4° C. The GST-fusion protein was subsequently affinity purified from the supernatant by glutathione agarose.

Baculovirus Expressed Cdk5/p35$^{nck5a}$ Complex

Sf21 insect cells were grown in 100 ml suspension culture until the density reached $1\times10^6$/ml to give a total of $1\times10^8$ cells. Recombinant baculovirus were added into culture according to the MOI ratio of 5:20 for Cdk5:p35$^{nck5a}$ On the 5th day of infection, cells were harvested by centrifugation at 500–700 rpm for 10 minutes and washed with two changes of PBS. Then the cell pellet was either stored at −80° C. or used directly for affinity binding assay.

Affinity Binding Assay

Glutathione agarose beads were washed with 1 ml washing buffer (MTPBS, 2 mM DTT), before the GST fusion protein was added to 40 µl of beads. The beads were mixed at 4° C. for one hour on a head-to-head mixer. The unbound protein was removed by washing the beads three times with 1 ml binding buffer (50 mM Tris-HCl pH 7.5, 1 mM EDTA, 1 mM EGTA, protease inhibitors cocktail i.e. 2 mM PMSF, 1 µg/ml leupeptin, 1 µg/ml antipain, 1 µg/ml aprotonin). The activator protein was then added and the binding was performed at a volume of 500 µl. After incubation at 4° C. for 1 hour, the beads were washed 5 times with 1 ml binding buffer and the proteins on the beads were released by addition of 40 µl of SDS loading buffer.

Immunoblotting

Proteins separated by SDS/PAGE were electrophoretically blotted onto PVDF membrane (Bio-Rad Laboratories, Canada) and probed with polyclonal anti-CDK5 or anti-p35 antibody (1:1000 dilution). Signal was detected with ECL Western blotting kit (Amersham Pharmacia Biotech) according to the supplier's protocol.

Results

Identification of Novel p35-association Protein

The yeast two-hybrid system is a sensitive method that provides a transcriptional assay for determining weak and transient protein-protein interactions. Using p35$^{nck5a}$ as bait, several cDNA sequences were isolated from a human brain cDNA library (Qi Z et al., 1998, supra).

As the cDNAs may encode proteins with transcriptional activation potential against the reporter genes resulting in false positives, the specificity of the detected interactions in the two-hybrid screen was analysed further. Different combinations of cotransformations, such as the library-isolated clones with the original bait, and the library-isolated clones with a hybrid construct of the DNA-binding domain with an unrelated protein, such as SNF1 or human Lamin C, was performed (Qi Z, 1996, Department of Biochemistry and Molecular Biology, University of Calgary, Calgary). The isolated clones that cause enhanced reporter activities when cotransformed with the original bait are considered as true positive clones. Among the positives are three sequences, designated as SEQ ID NO 2 (C42), SEQ ID NO 4 (C48), and SEQ ID NO 6 (C53), which do not match with a significant score to any other sequence in the GenBank/EMBL databases, indicating that these proteins are novel. The SEQ ID NO 4 (C48), SEQ ID NO 2 (C42), and SEQ ID NO 6 (C53), clones give a β-galactosidase activity of 40-, 11.8- and 13.4-fold higher than the control (a fragment of Lamin C) respectively (Table 1).

The partial cDNA sequences obtained from the yeast two-hybrid screening were used to synthesize probes for screening of the full length sequences from a rat brain cDNA library. After tertiary hybridisation, the well-isolated positive clones were picked and sequenced. The first methionine of a full length sequence was assigned based on the identification of a stop codon 5' upstream of an ATG start codon. All the full length sequences encompass the original partial cDNA sequence, although there are a low percentage of mutations (varies from 8–10%) at amino acid level for all three proteins. The chance that these mutations were introduced by cloning artefact is slim because of the fact that identical sequences were isolated from two separate rat brain cDNA libraries obtained from two different commercial sources for the three novel proteins. In fact, these mutations are most likely attributed to the difference in species used for constructing the cDNA library (human brain in yeast two-hybrid screening and rat brain in library screening).

Confirmation of Protein Binding Using Expressed Proteins

The full length proteins were expressed in GST fusion form for an in vitro binding assay. FIG. 1 shows that the GST fusion forms of each of the three novel proteins could co-precipitate with the bacterially expressed His-tagged p35$^{nck5a}$ protein and the baculovirus expressed p35$^{nck5a}$/Cdk5 protein complex. The difference in the amount of the protein co-precipitated was most likely due to the fact that the protein preparation contained various amount of the degraded form of the full length proteins.

Figure 2:
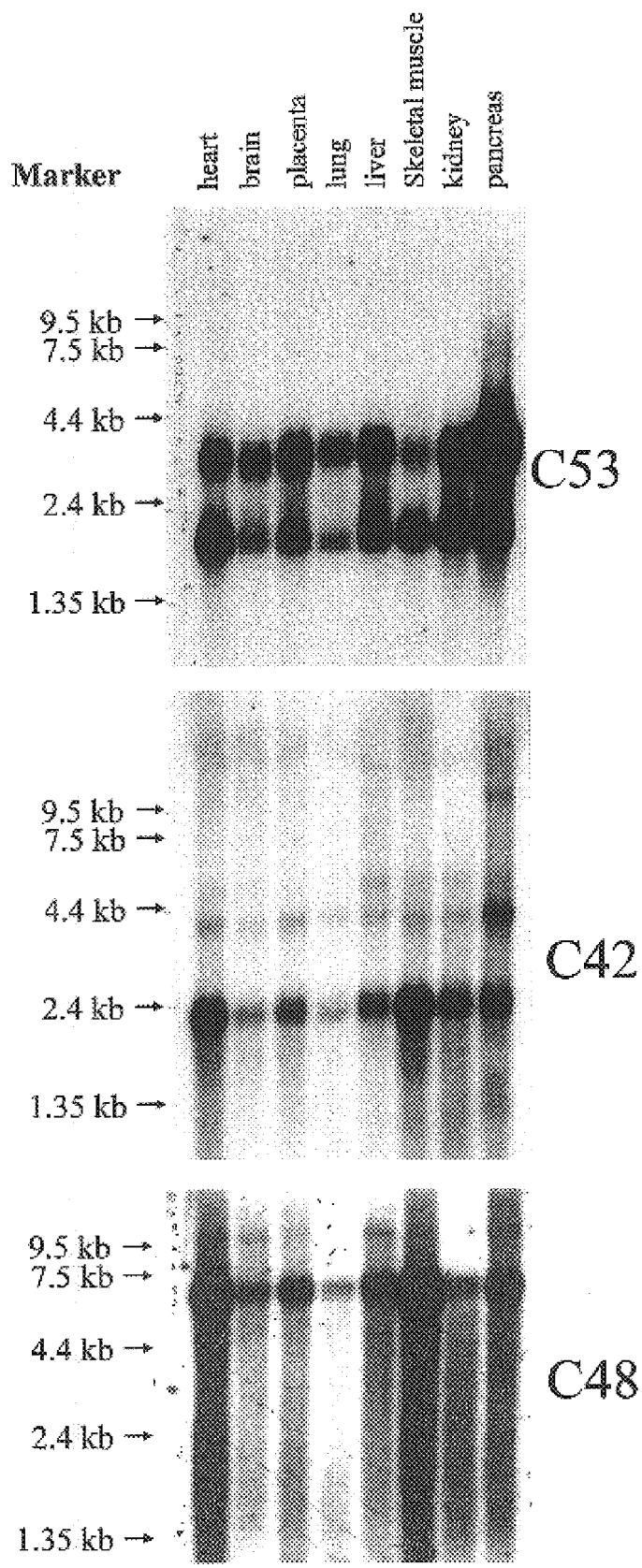
FIG. 2 shows Northern analysis of the novel p35 binding proteins. Lanes are (from left to right) molecular weight markers (9.5 kb, 7.5 kb, 4.4 kb, 2.4 kb and 1.35 kb) and messenger RNA from human heart, brain, placenta, lung, liver, skeletal muscle, kidney and pancreas was immobilised on nylon membrane and hybridised with specific probes derived from SEQ ID NO 6 (C53) (top gel), SEQ ID NO 2 (C42) (middle gel), and SEQ ID NO 4 (C48) (bottom gel) clones.

In order to examine the tissue distribution of these novel proteins, Northern analysis was performed. Equal amounts of mRNA (2 µg) extracted from different tissues were immobilised on a nylon membrane and hybridised with specific probe prepared from the novel clones. FIG. 2 showed that the mRNA of all three p35$^{nck5a}$ binding proteins were detected in a wide range of tissues, including heart, brain, placenta, lung, liver, skeletal, muscle, kidney and pancreas. Two major bands were seen in the SEQ ID NO 6 (C53) and SEQ ID NO 2 (C42) blots, whereas only one major band was seen in the SEQ ID NO 4 (C48) blot. The abundance of the mRNA transcripts of SEQ ID NO 6 (C53) is relatively constant in all the tissues examined. However, the transcripts of SEQ ID NO 2 (C42) and SEQ ID NO 6 (C48) seem to be lower in lung tissue, but higher in heart and skeletal muscle.

To study the effect of SEQ ID NO (C42), SEQ ID NO 4 (C48) and SEQ ID NO 6 (C53) on Cdk5 kinase activity, reconstituted GST-Cdk5/GST-p25 complexes were incubated with a range of concentrations of SEQ ID NO 2 (C42), SEQ ID NO 4 (C48) and SEQ ID NO 6 (C53) (FIG. 6). The results indicate that only a slight inhibition of the activity (up to about 20%) was observed with high concentrations of SEQ ID NO 4 (C48) and SEQ ID NO 6 (C53). Since each of SEQ ID NO 2 (C42), SEQ ID NO 4 (C48) and SEQ ID NO 6 (C53) possess the consensus phosphorylation site for Cdk5, which is a serine or threonine followed by a proline residue, the possibility that these proteins are substrates of Nclk was examined. The GST-fusion form of the proteins were incubated with the bacterially expressed GST-p25/GST-Cdk5 complex and tested for protein phosphorylation. To ensure that an equal amount of the active Cdk5 kinase complexes was used for the assay, the kinase was reconstituted in a large scale and aliquotted into each tube containing the GST-fusion proteins. The formation of complexes was confirmed by measuring the Cdk5 kinase activity using histone H1 peptides.

Figure 3:
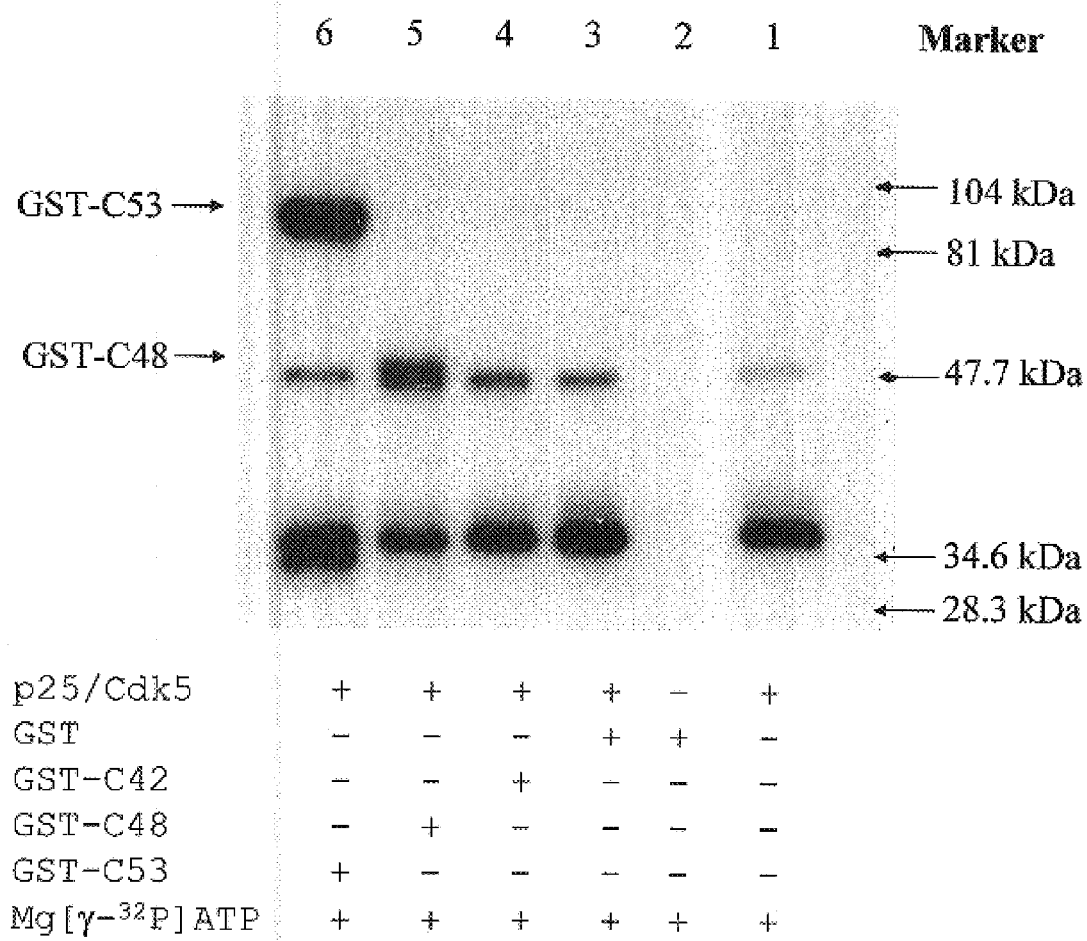
FIG. 3 shows phosphorylation of the novel p35 binding proteins by reconstituted Nclk. Ten µg of GST (lane 3), GST-C42 (SEQ ID NO 2) (lane 4), GST-C48 (SEQ ID NO 4) (lane 5) and GST-C53 (SEQ ID NO 6) (lane 6) were incubated with reconstituted Nclk (GST-p25/GST-Cdk5 complex) for one hour in the presence of $Mg[\gamma{-}^{32}P]$ ATP. Reconstituted Nclk (lane 1) and purified GST protein (lane 2) were included as controls. The proteins were separated in a 12% SDS PAGE gel and the autoradiograph was exposed for 3 hours at −80° C.

The autoradiograph in FIG. 3 indicated that the SEQ ID NO 4 (C48) and SEQ ID NO 6 (C53) proteins, but not the SEQ ID NO 2 (C42) protein, were phosphorylated by Cdk5 kinase. Two other phospholabelled band (~37 kDa and 50 kDa) were also seen in most of the lanes except the lane containing GST protein and $Mg[\gamma-^{32}P]ATP$ in the absence of p25/Cdk5. Most likely, these bands represented the phosphorylation of GST-p25 and its truncated form by Cdk5 kinase.

Results of Homology Search

In order to explore the biological function(s) of these novel proteins, the nucleotide and amino acid sequences of the full length proteins were submitted to the search engine (Blast program) in GenBank/EMBL, attempting to fish out any related protein(s). The search with the SEQ ID NO (C53) clone identified no known proteins apart from some expressed sequence tags (ESTs).

However, the homology search with the SEQ ID NO 2 (C42) clone identified homologues in *C. elegans* (41% identity) and *A. thaliana* (43% identity), suggesting that the protein is conserved during evolution (FIG. 4). The alignment of the three proteins, which was accomplished using the Clustal W (1.74) multiple sequence alignment program, showed a high homology within the core region of the proteins of about 300 amino acid residues, whereas both N-terminal and C-terminal regions are much more diverse. The function of these two homologues is unknown. More interesting results were observed in the homology search with the SEQ ID NO 4 (C48) clone sequence. The protein that has been identified is a recently discovered intermediate filament associated protein, called restin, which contains a SEQ ID NO 4 (C48) homology region ranging from amino acids 300 to 541 (~21% identity) (FIG. 5). The N-terminal serine-rich region of SEQ ID NO 4 (C48) (10 serine residues out of 28 amino acids) is also a common feature in a number of the intermediate filament proteins (type III and IV), e.g. neurofilament, vimentin and desmin. Within the serine-rich motif, there are two nclk phosphorylation sites, which may potentially be a target for the regulation of SEQ ID NO 4 (C48). The same motif of vimentin and desmin has been demonstrated to play an important role in the interaction of the N-terminal domain with other cytoskeletal components. This result suggests that the SEQ ID NO 4 (C48) protein may have function(s) involved in the structure of the cytoskeleton.

Conclusions

Thus the experiments detail the isolation and purification of three proteins—SEQ ID NO 2 (C42), SEQ ID NO 4 (C48) and SEQ ID NO 6 (C53)—which undergo high affinity association with both the free and the Cdk5 complexed forms of $p35^{nck5a}$.

The fact that full-length proteins (which are more likely to be the form present in cells) bind $p35^{nck5a}$ strongly, this suggests that they are nck5a binding proteins. This is further confirmed by the binding to the $Cdk5/p35^{nck5a}$ complex, which is necessary for any authentic Nck5a-binding protein since all $p25/35^{nck5a}$ in the cells appear to exist in complexes.

EXAMPLE 1

As detailed above, the proteins of the present invention are useful for affecting Cdk5 kinase activity. Briefly, reconstituted GST-Cdk5/GST-p25 complexes are incubated with SEQ ID NO 2 (C42), SEQ ID NO 4 (C48) or SEQ ID NO 6 (C53) at a desired concentration and the resulting activity of the kinase determined.

EXAMPLE 2

In order to identify substances, particularly proteins, which affect Cdk5 kinase activity, or to aid in the identification of the site at which a protein which affects Cdk5 kinase activity binds, or the mechanism by which they work, the assay of Example 1 for affecting Cdk5 kinase activity is performed with a range of concentrations of SEQ ID NO 2 (C42), SEQ ID NO 4 (C48) and SEQ ID NO 6 (C53), but the incubation step taking place in the presence of the substance or substances under investigation. Assay results are then correlated with results obtained without the substance(s) in order to determine whether or not the substance(s) affect Cdk5 kinase activity.

The assay of Example 2 is also useful in identifying proteins or other molecules or substances which affect the binding or action of SEQ ID NO 2 (C42), SEQ ID NO 4 (C48) and SEQ ID NO 6 (C53)—a change in the Cdk5 kinase activity during co-incubation with the protein/substance/molecule under investigation, particularly a failure of SEQ ID NO 2 (C42), SEQ ID NO 4 (C48) or SEQ ID NO 6 (C53) to cause the increase or decrease in Cdk5 kinase activity achieved in a control test, is indicative of its being affected by the test substance. SEQ ID NO 2 (C42) is a Cdk5 kinase inhibitor and may be used as described above to identify proteins or other molecules which affect the binding or activity of SEQ ID NO 2 (C42).

EXAMPLE 3

As detailed above, each of SEQ ID NO 2 (C42), SEQ ID NO 4 (C48) and SEQ ID NO 6 (C53) have high binding affinities for $p35^{nck5a}$, and they are therefore useful in isolating $p35^{nck5a}$ from a sample, or for detecting the presence of $p35^{nck5a}$ in a sample, for example as a concentration step in the screening of a large sample volume. In order to achieve this, an assay is performed as detailed above and shown in FIG. 1. SEQ ID NO 2 (C42), SEQ ID NO 4 (C48) or SEQ ID NO 6 (C53) hybridised (for example in the form of a GST fusion protein) to a solid support such as beads is contacted with a sample under conditions which allow specific binding of $p35^{nck5a}$. Any binding to the SEQ ID NO 2 (C42)/SEQ ID NO 4 (C48) SEQ ID NO 6 (C53) is then determined, and this is correlated with the presence in the sample of p35$^{nck5a}$.

EXAMPLE 4

The proteins of the present invention are also useful in purify molecules or compounds to which they can form complexes by specific binding (i.e. binding partners), particularly p35$^{nck5a}$. In order to purify a SEQ ID NO 2 (C42)/SEQ ID NO 4 (C48)/SEQ ID NO 6 (C53) binding partner, particularly p35$^{nck5a}$, from a sample, the SEQ ID NO 2 (C42)/SEQ ID NO 4 (C48)/SEQ ID NO 6 (C53) is contacted with a sample under conditions to allow specific binding. The SEQ ID NO 2 (C42)/SEQ ID NO 4 (C48)/SEQ ID NO 6 (C53) is then recoveredbound to the molecule or compound, and the SEQ ID NO 2 (C42)/SEQ ID NO 4 (C48) SEQ ID NO 6 (C53) is then separated from the molecule or compound, thereby obtaining purified molecule or compound.

Thus a method for screening a large number of molecules or compounds for their ability to form complexes with the p35$^{nck5a}$ binding protein of the present invention (particularly SEQ ID NO 2 (C42), SEQ ID NO 4 (C48) or SEQ ID NO 6 (C53)) comprises:

a) combining the p35$^{nck5a}$ binding protein of the invention with the compound or molecule under conditions to allow complex formation; and b) determining complex formation, wherein the presence of the complex identifies a molecule or compound that specifically binds the p35$^{nck5a}$ binding protein of the invention.

In particular, the molecule or compound is chosen from the group consisting of peptides, agonists, antagonists, inhibitors, antibodies and pharmaceutical agents (Remington's Pharmaceutical Sciences and US Pharmacopeia, 1984, Mack Publishing Company, Easton, Pa., USA; United States Pharmocopeia, ISBN: 1889788031). The preparation of inhibitors and antibodies (and antigen binding fragments thereof) is well known in the art and includes receptor blocking agents, receptor binding inhibitors, antisense oligonucleotides, and ribozymes (Harlow, E. and Lane, D., "Using Antibodies: A Laboratory Manual", Cold Spring Harbor Laboratory Press, New York, 1998; Rossi, J. J., 1999, Chemistry & Biology, 6: R33–R37).

TABLE 1

Yeast two-hybrid analysis of p35 associated protein

| Library cDNA/activation domain hybrid | Protein moiety in DNA binding domain | β-Galactosidase activity (Miller Units) |
|---|---|---|
| SEQ ID NO 2 (C42) | Lamin C | 1.7 |
| | P35 | 20.1 |
| SEQ ID NO 4 (C48) | Lamin C | 1.0 |
| | P35 | 40.2 |
| SEQ ID NO 6 (C53) | Lamin C | 1.0 |
| | P35 | 13.4 |

The activation domain of the hybrid was fused to the partial cDNA of SEQ ID NO 2 (C42), SEQ ID NO 4 (C48) and SEQ ID NO 6 (C53), and the binding domain was fused to the cDNA Of p35$^{nck5a}$. The β-galactosidase activity was measured after transformation and the cDNA of a fragment of Lamin C was used as a control.

What is claimed is:

1. A p35$^{nck5a}$ binding protein comprising the sequence selected from the group consisting of SEQ ID NOs: 2, 4 and 6.

2. The p35$^{nck5a}$ binding protein according to claim 1, wherein said p35$^{nck5a}$ binding protein has the consensus phosphorylation site for Cdk5.

3. A p35$^{nck5a}$ binding protein comprising the sequence of SEQ ID NO: 2 wherein said protein is a Cdk5 kinase inhibitor.

4. A p35$^{nck5a}$ binding protein comprising the sequence of SEQ ID NO 2.

5. A p35$^{nck5a}$ binding protein comprising the sequence of SEQ ID NO 4.

6. A p35$^{nck5a}$ binding protein comprising the sequence of SEQ ID NO 6.

* * * * *

SEQUENCE LISTING

<160> NUMBER OF SEQ ID NOS:   11

<210> SEQ ID NO 1
<211> LENGTH: 2592
<212> TYPE: DNA
<213> ORGANISM: Rattus norvegicus
<220> FEATURE:
<221> NAME/KEY: CDS
<222> LOCATION: (43)..(1803)

<400> SEQUENCE: 1

```
gcggacctcg cagttgtggg agattaagga ctgcacggtg cc atg cat cct tta        54
                                                 Met His Pro Leu
                                                  1 cag cgt gtc ttc cga gca cag agg cta tca gca cca ttg acc tcc atg     102
Gln Arg Val Phe Arg Ala Gln Arg Leu Ser Ala Pro Leu Thr Ser Met
 5              10                  15                  20 tgc tgg gtg ttg ctt agg acc ttc agg gca cat aac agc act tcc tgt     150
Cys Trp Val Leu Leu Arg Thr Phe Arg Ala His Asn Ser Thr Ser Cys
                25                  30                  35 cct gat cca gag ggg aag agc tca gaa gga gtt cag aag gat ttc agc     198
Pro Asp Pro Glu Gly Lys Ser Ser Glu Gly Val Gln Lys Asp Phe Ser
            40                  45                  50 tcc agg cta gcc act gga ccg act ttt cag cat ttt tta aga agt gct     246
Ser Arg Leu Ala Thr Gly Pro Thr Phe Gln His Phe Leu Arg Ser Ala
        55                  60                  65 tca gtt cct caa gag aaa cca tct tct cca gaa gtg gag gac cca cct     294
Ser Val Pro Gln Glu Lys Pro Ser Ser Pro Glu Val Glu Asp Pro Pro
    70                  75                  80
```

```
ccc tat ctc tca ggg gat gaa ctt cta gga agg cag aga aag gtc tac      342
Pro Tyr Leu Ser Gly Asp Glu Leu Leu Gly Arg Gln Arg Lys Val Tyr
 85                  90                  95                 100 ctc gag acc tat ggc tgt cag atg aat gtg aat gac aca gag ata gcc      390
Leu Glu Thr Tyr Gly Cys Gln Met Asn Val Asn Asp Thr Glu Ile Ala
                    105                 110                 115 tgg tcc att tta cag aag agc ggc tac ttg cgg acc agc aac ctt caa      438
Trp Ser Ile Leu Gln Lys Ser Gly Tyr Leu Arg Thr Ser Asn Leu Gln
                120                 125                 130 gag gcc gat gtg atc ctt ctt gtc acg tgt tct atc agg gag aag gct      486
Glu Ala Asp Val Ile Leu Leu Val Thr Cys Ser Ile Arg Glu Lys Ala
            135                 140                 145 gag cag acc atc tgg aac cgt tta cat cag cta aaa gtc ctg aag gca      534
Glu Gln Thr Ile Trp Asn Arg Leu His Gln Leu Lys Val Leu Lys Ala
        150                 155                 160 aag cga cca cgc tcc cgg gta cct ctg agg att ggg att cta ggc tgc      582
Lys Arg Pro Arg Ser Arg Val Pro Leu Arg Ile Gly Ile Leu Gly Cys
165                 170                 175                 180 atg gct gag aga ctg aag gga gag atc ctc aac agg gag aaa atg gta      630
Met Ala Glu Arg Leu Lys Gly Glu Ile Leu Asn Arg Glu Lys Met Val
                    185                 190                 195 gat ctt ttg gct ggt cca gat gcc tat cga gac ctt ccc cgg ctg ctg      678
Asp Leu Leu Ala Gly Pro Asp Ala Tyr Arg Asp Leu Pro Arg Leu Leu
                200                 205                 210 gcc gtt gtg gag tca ggt cag caa gca gca aat gtg ctt ctc tct ctg      726
Ala Val Val Glu Ser Gly Gln Gln Ala Ala Asn Val Leu Leu Ser Leu
            215                 220                 225 gat gag acc tac gcg gat atc atg cca gtc caa acg agc ccc agt gcc      774
Asp Glu Thr Tyr Ala Asp Ile Met Pro Val Gln Thr Ser Pro Ser Ala
        230                 235                 240 act tct gcc ttc gtg tca atc atg cgg ggc tgc gac aat atg tgc agt      822
Thr Ser Ala Phe Val Ser Ile Met Arg Gly Cys Asp Asn Met Cys Ser
245                 250                 255                 260 tac tgt atc gtt cct ttc act cgg ggc agg gag agg agt cgg cca gtt      870
Tyr Cys Ile Val Pro Phe Thr Arg Gly Arg Glu Arg Ser Arg Pro Val
                    265                 270                 275 gcc tcc att cta gat gaa gtg agg aag ctc tct gag cag ggg cta aaa      918
Ala Ser Ile Leu Asp Glu Val Arg Lys Leu Ser Glu Gln Gly Leu Lys
                280                 285                 290 gaa gtg aca ctt cta ggt cag aat gtt aat agt ttt cgg gac aat tca      966
Glu Val Thr Leu Leu Gly Gln Asn Val Asn Ser Phe Arg Asp Asn Ser
            295                 300                 305 gaa gtc cag ttc agt agt aca ggg tct gcc aac ctc agc cgt ggc ttt     1014
Glu Val Gln Phe Ser Ser Thr Gly Ser Ala Asn Leu Ser Arg Gly Phe
        310                 315                 320 act acc aac tat aaa ccc aaa caa gga ggg ctt cgt ttt tct cac ctt     1062
Thr Thr Asn Tyr Lys Pro Lys Gln Gly Gly Leu Arg Phe Ser His Leu
325                 330                 335                 340 ctg gat cag gtt tca aga ata gat cct gaa atg agg att cgt ttc acc     1110
Leu Asp Gln Val Ser Arg Ile Asp Pro Glu Met Arg Ile Arg Phe Thr
                    345                 350                 355 tct cct cac ccc aag gat ttt ccc gat gag gtt cta cag ctg att cgt     1158
Ser Pro His Pro Lys Asp Phe Pro Asp Glu Val Leu Gln Leu Ile Arg
                360                 365                 370 gag aga cac aac atc tgt aag cag atc cac ctg cca gcc cag agt ggg     1206
Glu Arg His Asn Ile Cys Lys Gln Ile His Leu Pro Ala Gln Ser Gly
            375                 380                 385 agc agc cgt gta ctg gag gcc atg cgg aga gga tat tca aga gaa gca     1254
Ser Ser Arg Val Leu Glu Ala Met Arg Arg Gly Tyr Ser Arg Glu Ala
```

```
                390             395             400
tac gtg gct ttg gtt cat cat atc agg gag gct atc cca ggt gtg ggc    1302
Tyr Val Ala Leu Val His His Ile Arg Glu Ala Ile Pro Gly Val Gly
405                 410                 415                 420 ctc agc agc gac ttc atc act ggc ttc tgt gga gag aca gag gac gat    1350
Leu Ser Ser Asp Phe Ile Thr Gly Phe Cys Gly Glu Thr Glu Asp Asp
                425                 430                 435 cac ctg cag aca gtg tct tta ctt cga gaa gtt cag tac aat act ggt    1398
His Leu Gln Thr Val Ser Leu Leu Arg Glu Val Gln Tyr Asn Thr Gly
            440                 445                 450 ttt ctc ttt gca tac agc atg agg caa aag aca cga gca tat cat agg    1446
Phe Leu Phe Ala Tyr Ser Met Arg Gln Lys Thr Arg Ala Tyr His Arg
        455                 460                 465 ctg aag gat gac gtt cca gaa gaa gta aaa tta agg cgt ttg gag gaa    1494
Leu Lys Asp Asp Val Pro Glu Glu Val Lys Leu Arg Arg Leu Glu Glu
470                 475                 480 ctt att act gtc ttc cga gaa gaa gct tca aaa gtc aat gcg acc tca    1542
Leu Ile Thr Val Phe Arg Glu Glu Ala Ser Lys Val Asn Ala Thr Ser
485                 490                 495                 500 gtg ggt tgt acc cag ctg gta ttg gtt gaa ggg ttc agc aag cgt tct    1590
Val Gly Cys Thr Gln Leu Val Leu Val Glu Gly Phe Ser Lys Arg Ser
                505                 510                 515 acc aca gac ctg tgt ggc cga aat gat gca aac ctt aag gtg att ttc    1638
Thr Thr Asp Leu Cys Gly Arg Asn Asp Ala Asn Leu Lys Val Ile Phe
            520                 525                 530 cct gat gcc gag gtg gag gat atc act gac cct ggg ctc aag gtc aga    1686
Pro Asp Ala Glu Val Glu Asp Ile Thr Asp Pro Gly Leu Lys Val Arg
        535                 540                 545 gct cag cct ggg gac tat gtg ctg gtg aag atc atc tct gcc agt tct    1734
Ala Gln Pro Gly Asp Tyr Val Leu Val Lys Ile Ile Ser Ala Ser Ser
550                 555                 560 caa act ctc aaa gga cac att ctc tgc agg acc act atg aaa gac tca    1782
Gln Thr Leu Lys Gly His Ile Leu Cys Arg Thr Thr Met Lys Asp Ser
565                 570                 575                 580 tca atg aat tgc ttg acc tga gttggtggct tagtggtgga cttgggcagt       1833
Ser Met Asn Cys Leu Thr
                585 tttttctcat gctttggaga caaggagttc cagttttcaa cctggaggtt caggcttggg  1893 agctggtgga agacgaagtt ccaggaggca gcagatacac aggaagcgtg aggctgaccc  1953 tggcttgttc agaagcgtct cttccttcag ccaacagaac aaatcagcag cgaaaattca  2013 caggatttgg tgggatatgt tagagaagac taggttctct attttaagat ttttttttt   2073 taaatttatg tgtatgtgag catgtgcttt ggcagccaga gggcgccaga gtccctggaa  2133 ctgtagttac acatgggtgt gagtgcttga tataggttct aggtcctctg tgagagcagt  2193 ggatgttttt aatctctgac ccacctctcc atctcaaagg tgaagttgtt tgtttgtttt  2253 tttaaattta atgtgtgggt gttttgcctg tatttatctc agtatgacaa tacatatgct  2313 tggcacacac taggccggaa gaaggcacag gtcccctggc actggagatc cagttgtgag  2373 ccatgatgtg ggttctggga actgaaccag ctcctctggg agggcagcca gtgtcctcac  2433 catggatctc tctctccagc tcaagccttg ttttgaaacg tgttcttgtg atgatgccta  2493 ggttggtctc caactaataa tcctcctgtc gcagccttct gaggagctag agtcatacag  2553 atgggtgtca cttaggggta gtttataagg tataacctg                        2592

<210> SEQ ID NO 2
<211> LENGTH: 586
```

```
<212> TYPE: PRT
<213> ORGANISM: Rattus norvegicus

<400> SEQUENCE: 2

Met His Pro Leu Gln Arg Val Phe Arg Ala Gln Arg Leu Ser Ala Pro
1               5                   10                  15

Leu Thr Ser Met Cys Trp Val Leu Leu Arg Thr Phe Arg Ala His Asn
            20                  25                  30

Ser Thr Ser Cys Pro Asp Pro Glu Gly Lys Ser Ser Glu Gly Val Gln
        35                  40                  45

Lys Asp Phe Ser Ser Arg Leu Ala Thr Gly Pro Thr Phe Gln His Phe
50                  55                  60

Leu Arg Ser Ala Ser Val Pro Gln Glu Lys Pro Ser Ser Pro Glu Val
65                  70                  75                  80

Glu Asp Pro Pro Tyr Leu Ser Gly Asp Glu Leu Leu Gly Arg Gln
                85                  90                  95

Arg Lys Val Tyr Leu Glu Thr Tyr Gly Cys Gln Met Asn Val Asn Asp
                100                 105                 110

Thr Glu Ile Ala Trp Ser Ile Leu Gln Lys Ser Gly Tyr Leu Arg Thr
            115                 120                 125

Ser Asn Leu Gln Glu Ala Asp Val Ile Leu Val Thr Cys Ser Ile
        130                 135                 140

Arg Glu Lys Ala Glu Gln Thr Ile Trp Asn Arg Leu His Gln Leu Lys
145                 150                 155                 160

Val Leu Lys Ala Lys Arg Pro Arg Ser Arg Val Pro Leu Arg Ile Gly
                165                 170                 175

Ile Leu Gly Cys Met Ala Glu Arg Leu Lys Gly Glu Ile Leu Asn Arg
            180                 185                 190

Glu Lys Met Val Asp Leu Leu Ala Gly Pro Asp Ala Tyr Arg Asp Leu
        195                 200                 205

Pro Arg Leu Leu Ala Val Val Glu Ser Gly Gln Gln Ala Ala Asn Val
        210                 215                 220

Leu Leu Ser Leu Asp Glu Thr Tyr Ala Asp Ile Met Pro Val Gln Thr
225                 230                 235                 240

Ser Pro Ser Ala Thr Ser Ala Phe Val Ser Ile Met Arg Gly Cys Asp
                245                 250                 255

Asn Met Cys Ser Tyr Cys Ile Val Pro Phe Thr Arg Gly Arg Glu Arg
            260                 265                 270

Ser Arg Pro Val Ala Ser Ile Leu Asp Glu Val Arg Lys Leu Ser Glu
        275                 280                 285

Gln Gly Leu Lys Glu Val Thr Leu Leu Gly Gln Asn Val Asn Ser Phe
    290                 295                 300

Arg Asp Asn Ser Glu Val Gln Phe Ser Ser Thr Gly Ser Ala Asn Leu
305                 310                 315                 320

Ser Arg Gly Phe Thr Thr Asn Tyr Lys Pro Lys Gln Gly Gly Leu Arg
                325                 330                 335

Phe Ser His Leu Leu Asp Gln Val Ser Arg Ile Asp Pro Glu Met Arg
            340                 345                 350

Ile Arg Phe Thr Ser Pro His Pro Lys Asp Phe Pro Asp Glu Val Leu
        355                 360                 365

Gln Leu Ile Arg Glu Arg His Asn Ile Cys Lys Gln Ile His Leu Pro
    370                 375                 380

Ala Gln Ser Gly Ser Ser Arg Val Leu Glu Ala Met Arg Arg Gly Tyr
385                 390                 395                 400
```

-continued

```
Ser Arg Glu Ala Tyr Val Ala Leu Val His His Ile Arg Glu Ala Ile
            405                 410                 415

Pro Gly Val Gly Leu Ser Ser Asp Phe Ile Thr Gly Phe Cys Gly Glu
        420                 425                 430

Thr Glu Asp Asp His Leu Gln Thr Val Ser Leu Leu Arg Glu Val Gln
    435                 440                 445

Tyr Asn Thr Gly Phe Leu Phe Ala Tyr Ser Met Arg Gln Lys Thr Arg
    450                 455                 460

Ala Tyr His Arg Leu Lys Asp Val Pro Glu Glu Val Lys Leu Arg
465                 470                 475                 480

Arg Leu Glu Glu Leu Ile Thr Val Phe Arg Glu Ala Ser Lys Val
            485                 490                 495

Asn Ala Thr Ser Val Gly Cys Thr Gln Leu Val Leu Val Glu Gly Phe
        500                 505                 510

Ser Lys Arg Ser Thr Thr Asp Leu Cys Gly Arg Asn Asp Ala Asn Leu
    515                 520                 525

Lys Val Ile Phe Pro Asp Ala Glu Val Glu Asp Ile Thr Asp Pro Gly
530                 535                 540

Leu Lys Val Arg Ala Gln Pro Gly Asp Tyr Val Leu Val Lys Ile Ile
545                 550                 555                 560

Ser Ala Ser Ser Gln Thr Leu Lys Gly His Ile Leu Cys Arg Thr Thr
            565                 570                 575

Met Lys Asp Ser Ser Met Asn Cys Leu Thr
        580                 585

<210> SEQ ID NO 3
<211> LENGTH: 657
<212> TYPE: DNA
<213> ORGANISM: Rattus norvegicus
<220> FEATURE:
<221> NAME/KEY: CDS
<222> LOCATION: (1)..(657)

<400> SEQUENCE: 3 atg gca cct aaa tca gct tct gag act cct gtc ctt tct gga act gat      48
Met Ala Pro Lys Ser Ala Ser Glu Thr Pro Val Leu Ser Gly Thr Asp
1               5                   10                  15 gtt gat tcc ctc tcc tgt gac agt acc agt tct gcc acc agc cca tct     96
Val Asp Ser Leu Ser Cys Asp Ser Thr Ser Ser Ala Thr Ser Pro Ser
            20                  25                  30 tgc atg ccc tgc ctg gtt gct ggc cgc cac ctg tgg gcc agc aag agt    144
Cys Met Pro Cys Leu Val Ala Gly Arg His Leu Trp Ala Ser Lys Ser
        35                  40                  45 ggc cac cac atg ctg tgc ctg att gag gac tat gat gcc ctc tat aag    192
Gly His His Met Leu Cys Leu Ile Glu Asp Tyr Asp Ala Leu Tyr Lys
    50                  55                  60 cag atc agc tgg ggc cag aca ctg ctt gcc aag atg gat att caa acc    240
Gln Ile Ser Trp Gly Gln Thr Leu Leu Ala Lys Met Asp Ile Gln Thr
65                  70                  75                  80 caa gag gct ctg agc ccc aca agt cag aag ctg gga cca aag gct tca    288
Gln Glu Ala Leu Ser Pro Thr Ser Gln Lys Leu Gly Pro Lys Ala Ser
                85                  90                  95 ttc tct gtg cct ctg agc aag ttt ctc tcc agc atg aac aca gcc aag    336
Phe Ser Val Pro Leu Ser Lys Phe Leu Ser Ser Met Asn Thr Ala Lys
            100                 105                 110 ctg atc ctg gaa aaa gcc tcc agg ttg ctg aag ctc ttc tgg agg gtc    384
Leu Ile Leu Glu Lys Ala Ser Arg Leu Leu Lys Leu Phe Trp Arg Val
        115                 120                 125
```

```
tct gtc ccc acc aac ggc cag tgt tcc ctt cac tgt gac cag att gga      432
Ser Val Pro Thr Asn Gly Gln Cys Ser Leu His Cys Asp Gln Ile Gly
    130                 135                 140 gaa atg aag gca gag atc acc aaa cta cac aaa aaa ttg ttt gaa caa      480
Glu Met Lys Ala Glu Ile Thr Lys Leu His Lys Lys Leu Phe Glu Gln
145                 150                 155                 160 gaa aag aag ctg cag aac aca gca aaa ctt ctg cag cag agc aag cac      528
Glu Lys Lys Leu Gln Asn Thr Ala Lys Leu Leu Gln Gln Ser Lys His
                165                 170                 175 cag gag aaa atc atc ttt gat cag ttg gtc atc acc cac caa gtc ctt      576
Gln Glu Lys Ile Ile Phe Asp Gln Leu Val Ile Thr His Gln Val Leu
            180                 185                 190 cgg aaa gcc agg gga aac ctg gag ctc agg cct aga gct gcc cat cca      624
Arg Lys Ala Arg Gly Asn Leu Glu Leu Arg Pro Arg Ala Ala His Pro
        195                 200                 205 gga aca tcc agt ccc agc aga ccg ggc tca tga                          657
Gly Thr Ser Ser Pro Ser Arg Pro Gly Ser
    210                 215
```

<210> SEQ ID NO 4
<211> LENGTH: 218
<212> TYPE: PRT
<213> ORGANISM: Rattus norvegicus

<400> SEQUENCE: 4

```
Met Ala Pro Lys Ser Ala Ser Glu Thr Pro Val Leu Ser Gly Thr Asp
1               5                   10                  15

Val Asp Ser Leu Ser Cys Asp Ser Thr Ser Ser Ala Thr Ser Pro Ser
                20                  25                  30

Cys Met Pro Cys Leu Val Ala Gly Arg His Leu Trp Ala Ser Lys Ser
            35                  40                  45

Gly His His Met Leu Cys Leu Ile Glu Asp Tyr Asp Ala Leu Tyr Lys
        50                  55                  60

Gln Ile Ser Trp Gly Gln Thr Leu Leu Ala Lys Met Asp Ile Gln Thr
65                  70                  75                  80

Gln Glu Ala Leu Ser Pro Thr Ser Gln Lys Leu Gly Pro Lys Ala Ser
                85                  90                  95

Phe Ser Val Pro Leu Ser Lys Phe Leu Ser Ser Met Asn Thr Ala Lys
            100                 105                 110

Leu Ile Leu Glu Lys Ala Ser Arg Leu Leu Lys Leu Phe Trp Arg Val
        115                 120                 125

Ser Val Pro Thr Asn Gly Gln Cys Ser Leu His Cys Asp Gln Ile Gly
    130                 135                 140

Glu Met Lys Ala Glu Ile Thr Lys Leu His Lys Lys Leu Phe Glu Gln
145                 150                 155                 160

Glu Lys Lys Leu Gln Asn Thr Ala Lys Leu Leu Gln Gln Ser Lys His
                165                 170                 175

Gln Glu Lys Ile Ile Phe Asp Gln Leu Val Ile Thr His Gln Val Leu
            180                 185                 190

Arg Lys Ala Arg Gly Asn Leu Glu Leu Arg Pro Arg Ala Ala His Pro
        195                 200                 205

Gly Thr Ser Ser Pro Ser Arg Pro Gly Ser
    210                 215
```

<210> SEQ ID NO 5
<211> LENGTH: 1865
<212> TYPE: DNA

<213> ORGANISM: Rattus norvegicus
<220> FEATURE:
<221> NAME/KEY: CDS
<222> LOCATION: (88)..(1602)

<400> SEQUENCE: 5

```
cggcacgagc tgaattgagg ctcaggcacg ccggctcagg attggtgctg ggccgggccg     60
gggtctttgg ccggaagtgg aaaaagg atg cag gac cat cag cac gtg ccc atc    114
                                Met Gln Asp His Gln His Val Pro Ile
                                  1               5 gac atc cag acc agc aag ctg ctc gat tgg ctg gtg gac aga aga cac      162
Asp Ile Gln Thr Ser Lys Leu Leu Asp Trp Leu Val Asp Arg Arg His
 10              15                  20                  25 tgc aac tta aaa tgg caa agc ctg gtg ctg acc atc cgg gaa aag atc      210
Cys Asn Leu Lys Trp Gln Ser Leu Val Leu Thr Ile Arg Glu Lys Ile
             30                  35                  40 aac acc gcc atc cag gac atg cca gag agc caa gag att gcc cag ctg      258
Asn Thr Ala Ile Gln Asp Met Pro Glu Ser Gln Glu Ile Ala Gln Leu
         45                  50                  55 ctc tct ggt tcc tac atc cac tac ttc cac tgc cta aga ata gtg gac      306
Leu Ser Gly Ser Tyr Ile His Tyr Phe His Cys Leu Arg Ile Val Asp
     60                  65                  70 ctt ctt aaa ggt acc gag gct tcc acc aaa aat att ttt ggc cgc tac      354
Leu Leu Lys Gly Thr Glu Ala Ser Thr Lys Asn Ile Phe Gly Arg Tyr
 75                  80                  85 tct tca cag cgg atg aag gat tgg cag gag atc ata agc ctg tat gag      402
Ser Ser Gln Arg Met Lys Asp Trp Gln Glu Ile Ile Ser Leu Tyr Glu
 90                  95                 100                 105 aag gac aac acc tat tta gtg gaa ctc tct agc ctc ctg gtt cgg aat      450
Lys Asp Asn Thr Tyr Leu Val Glu Leu Ser Ser Leu Leu Val Arg Asn
                110                 115                 120 gtc aac tat gag atc ccc tct ctg aag aag cag att gcc aag tgc cag      498
Val Asn Tyr Glu Ile Pro Ser Leu Lys Lys Gln Ile Ala Lys Cys Gln
            125                 130                 135 caa ctg cag caa gac tac agc cgc aag gag gag gag ggc cag gct ggg      546
Gln Leu Gln Gln Asp Tyr Ser Arg Lys Glu Glu Glu Gly Gln Ala Gly
        140                 145                 150 gct gct gag atg cga gag cag ttc tac cac tcc tgc aaa cag tac ggc      594
Ala Ala Glu Met Arg Glu Gln Phe Tyr His Ser Cys Lys Gln Tyr Gly
    155                 160                 165 atc acg gga gac aat gtc cga cga gag ctt ctg gcc ctg gtg aag gac      642
Ile Thr Gly Asp Asn Val Arg Arg Glu Leu Leu Ala Leu Val Lys Asp
170                 175                 180                 185 ctg cca agt cag ctg gct gag ata gga gcg gga gct cag tcc ctg ggg      690
Leu Pro Ser Gln Leu Ala Glu Ile Gly Ala Gly Ala Gln Ser Leu Gly
                190                 195                 200 gaa gcc atc gac ctg tac cag gcc tgt gtg gag ttt gta tgt gac agc      738
Glu Ala Ile Asp Leu Tyr Gln Ala Cys Val Glu Phe Val Cys Asp Ser
            205                 210                 215 ccc aca gag cag gtg ctg ccc atg ctg cgg tac gtt cag ccg aag gga      786
Pro Thr Glu Gln Val Leu Pro Met Leu Arg Tyr Val Gln Pro Lys Gly
        220                 225                 230 aac tcc acg gtg tat gag tgg agg aca ggg aca gag ccc tct gtg gta      834
Asn Ser Thr Val Tyr Glu Trp Arg Thr Gly Thr Glu Pro Ser Val Val
    235                 240                 245 gag cgg cca caa ctg gag gac cct ccc gag cag gtg caa gaa gac gag      882
Glu Arg Pro Gln Leu Glu Asp Pro Pro Glu Gln Val Gln Glu Asp Glu
250                 255                 260                 265 atc gac tgg ggc gac ttt ggc ctg gag gct gtt tct gac tct gga aac      930
Ile Asp Trp Gly Asp Phe Gly Leu Glu Ala Val Ser Asp Ser Gly Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 270 |     |     |     |     | 275 |     |     |     |     | 280 |      |
| atc | atc | tct | gct | gag | acc | cct | ggg | ata | gac | tgg | ggt | atc | tcc | ctg | gag | 978  |
| Ile | Ile | Ser | Ala | Glu | Thr | Pro | Gly | Ile | Asp | Trp | Gly | Ile | Ser | Leu | Glu |      |
|     |     |     |     | 285 |     |     |     |     | 290 |     |     |     |     | 295 |     |      |
| tca | gag | tcc | aag | gat | gct | ggg | gct | gac | aag | ata | gac | tgg | ggt | gac | aat | 1026 |
| Ser | Glu | Ser | Lys | Asp | Ala | Gly | Ala | Asp | Lys | Ile | Asp | Trp | Gly | Asp | Asn |      |
|     |     |     | 300 |     |     |     |     | 305 |     |     |     |     | 310 |     |     |      |
| gct | gtt | gct | tcg | gag | atc | acc | gtg | ctg | gag | aca | gga | acg | gag | gct | cca | 1074 |
| Ala | Val | Ala | Ser | Glu | Ile | Thr | Val | Leu | Glu | Thr | Gly | Thr | Glu | Ala | Pro |      |
|     | 315 |     |     |     |     | 320 |     |     |     |     | 325 |     |     |     |     |      |
| gag | ggt | gtt | gct | agg | ggc | tca | gac | gct | ctg | act | ctc | ctt | gaa | tac | cct | 1122 |
| Glu | Gly | Val | Ala | Arg | Gly | Ser | Asp | Ala | Leu | Thr | Leu | Leu | Glu | Tyr | Pro |      |
| 330 |     |     |     |     | 335 |     |     |     |     | 340 |     |     |     |     | 345 |      |
| gag | act | cgg | aat | cag | ttc | atc | gat | gag | ctc | atg | gag | ctt | gag | atc | ttc | 1170 |
| Glu | Thr | Arg | Asn | Gln | Phe | Ile | Asp | Glu | Leu | Met | Glu | Leu | Glu | Ile | Phe |      |
|     |     |     |     | 350 |     |     |     |     | 355 |     |     |     |     | 360 |     |      |
| ttg | tct | cag | aga | gca | gta | gag | atg | agt | gag | gag | gct | gac | atc | ctg | tcc | 1218 |
| Leu | Ser | Gln | Arg | Ala | Val | Glu | Met | Ser | Glu | Glu | Ala | Asp | Ile | Leu | Ser |      |
|     |     |     | 365 |     |     |     |     | 370 |     |     |     |     | 375 |     |     |      |
| gtg | agc | cag | ttc | cag | ctg | gct | cct | gcc | atc | ctt | cag | ggc | cag | acc | aag | 1266 |
| Val | Ser | Gln | Phe | Gln | Leu | Ala | Pro | Ala | Ile | Leu | Gln | Gly | Gln | Thr | Lys |      |
|     |     | 380 |     |     |     |     | 385 |     |     |     |     | 390 |     |     |     |      |
| gag | aag | atg | ctc | agc | ctg | gtg | tcc | aca | ctg | cag | cat | ctg | att | ggc | cag | 1314 |
| Glu | Lys | Met | Leu | Ser | Leu | Val | Ser | Thr | Leu | Gln | His | Leu | Ile | Gly | Gln |      |
| 395 |     |     |     |     | 400 |     |     |     |     | 405 |     |     |     |     |     |      |
| ctc | acc | agt | ctg | gac | ctg | cag | cac | ctg | ttt | atg | att | ctg | gcc | tca | ccg | 1362 |
| Leu | Thr | Ser | Leu | Asp | Leu | Gln | His | Leu | Phe | Met | Ile | Leu | Ala | Ser | Pro |      |
| 410 |     |     |     | 415 |     |     |     |     | 420 |     |     |     |     | 425 |     |      |
| agg | tat | gtg | gac | cgg | gtg | aca | gag | ctc | ctc | cag | cag | aag | ctg | aag | cag | 1410 |
| Arg | Tyr | Val | Asp | Arg | Val | Thr | Glu | Leu | Leu | Gln | Gln | Lys | Leu | Lys | Gln |      |
|     |     |     |     | 430 |     |     |     |     | 435 |     |     |     |     | 440 |     |      |
| tcc | cag | ctg | ttg | gct | ctg | aag | aag | gac | ctg | atg | gtg | gag | aag | cag | cag | 1458 |
| Ser | Gln | Leu | Leu | Ala | Leu | Lys | Lys | Asp | Leu | Met | Val | Glu | Lys | Gln | Gln |      |
|     |     |     | 445 |     |     |     |     | 450 |     |     |     |     | 455 |     |     |      |
| gag | gcg | ctt | cag | gag | cag | gca | gcg | ctg | gag | ccc | aag | ctg | gac | ctg | ctg | 1506 |
| Glu | Ala | Leu | Gln | Glu | Gln | Ala | Ala | Leu | Glu | Pro | Lys | Leu | Asp | Leu | Leu |      |
|     | 460 |     |     |     |     | 465 |     |     |     |     | 470 |     |     |     |     |      |
| ctg | gag | aag | acc | aga | gag | ctg | cag | aag | ctg | att | gaa | gct | gac | atc | tcc | 1554 |
| Leu | Glu | Lys | Thr | Arg | Glu | Leu | Gln | Lys | Leu | Ile | Glu | Ala | Asp | Ile | Ser |      |
| 475 |     |     |     |     | 480 |     |     |     |     | 485 |     |     |     |     |     |      |
| aag | aga | tac | aac | ggc | cgt | cct | gtg | aac | ctg | atg | ggg | acc | tct | gtg | tga | 1602 |
| Lys | Arg | Tyr | Asn | Gly | Arg | Pro | Val | Asn | Leu | Met | Gly | Thr | Ser | Val |     |      |
| 490 |     |     |     | 495 |     |     |     |     | 500 |     |     |     |     |     |     |      |

```
cgtgctggcc ctgtgtccgc caccagcggc ctggtggggg tggacagccc aggctggtat    1662
tgctggacct caccagcaag aagccagcag aggtggagca gagccacaag gaagcacctg    1722
agtggtggca ccagcattca ttgtgaccta tgcaagaagt ctgagtggct ctgtggatct    1782
aagcctaagg cacagttgct tcttctggtt atcaaggaag gcttaataaa aaaggaagt    1842 gactcctcaa aaaaaaaaaa aaa                                             1865
```

<210> SEQ ID NO 6
<211> LENGTH: 504
<212> TYPE: PRT
<213> ORGANISM: Rattus norvegicus

<400> SEQUENCE: 6

Met Gln Asp His Gln His Val Pro Ile Asp Ile Gln Thr Ser Lys Leu
1               5                   10                  15

-continued

```
Leu Asp Trp Leu Val Asp Arg Arg His Cys Asn Leu Lys Trp Gln Ser
             20                  25                  30

Leu Val Leu Thr Ile Arg Glu Lys Ile Asn Thr Ala Ile Gln Asp Met
         35                  40                  45

Pro Glu Ser Gln Glu Ile Ala Gln Leu Leu Ser Gly Ser Tyr Ile His
     50                  55                  60

Tyr Phe His Cys Leu Arg Ile Val Asp Leu Leu Lys Gly Thr Glu Ala
 65                  70                  75                  80

Ser Thr Lys Asn Ile Phe Gly Arg Tyr Ser Ser Gln Arg Met Lys Asp
                 85                  90                  95

Trp Gln Glu Ile Ile Ser Leu Tyr Glu Lys Asp Asn Thr Tyr Leu Val
             100                 105                 110

Glu Leu Ser Ser Leu Leu Val Arg Asn Val Asn Tyr Glu Ile Pro Ser
             115                 120                 125

Leu Lys Lys Gln Ile Ala Lys Cys Gln Gln Leu Gln Gln Asp Tyr Ser
     130                 135                 140

Arg Lys Glu Glu Glu Gly Gln Ala Gly Ala Ala Glu Met Arg Glu Gln
145                 150                 155                 160

Phe Tyr His Ser Cys Lys Gln Tyr Gly Ile Thr Gly Asp Asn Val Arg
                 165                 170                 175

Arg Glu Leu Leu Ala Leu Val Lys Asp Leu Pro Ser Gln Leu Ala Glu
             180                 185                 190

Ile Gly Ala Gly Ala Gln Ser Leu Gly Glu Ala Ile Asp Leu Tyr Gln
             195                 200                 205

Ala Cys Val Glu Phe Val Cys Asp Ser Pro Thr Glu Gln Val Leu Pro
     210                 215                 220

Met Leu Arg Tyr Val Gln Pro Lys Gly Asn Ser Thr Val Tyr Glu Trp
225                 230                 235                 240

Arg Thr Gly Thr Glu Pro Ser Val Val Glu Arg Pro Gln Leu Glu Asp
                 245                 250                 255

Pro Pro Glu Gln Val Gln Glu Asp Glu Ile Asp Trp Gly Asp Phe Gly
             260                 265                 270

Leu Glu Ala Val Ser Asp Ser Gly Asn Ile Ile Ser Ala Glu Thr Pro
             275                 280                 285

Gly Ile Asp Trp Gly Ile Ser Leu Glu Ser Glu Ser Lys Asp Ala Gly
     290                 295                 300

Ala Asp Lys Ile Asp Trp Gly Asp Asn Ala Val Ala Ser Glu Ile Thr
305                 310                 315                 320

Val Leu Glu Thr Gly Thr Glu Ala Pro Glu Gly Val Ala Arg Gly Ser
                 325                 330                 335

Asp Ala Leu Thr Leu Leu Glu Tyr Pro Glu Thr Arg Asn Gln Phe Ile
             340                 345                 350

Asp Glu Leu Met Glu Leu Glu Ile Phe Leu Ser Gln Arg Ala Val Glu
             355                 360                 365

Met Ser Glu Glu Ala Asp Ile Leu Ser Val Ser Gln Phe Gln Leu Ala
     370                 375                 380

Pro Ala Ile Leu Gln Gly Gln Thr Lys Glu Lys Met Leu Ser Leu Val
385                 390                 395                 400

Ser Thr Leu Gln His Leu Ile Gly Gln Leu Thr Ser Leu Asp Leu Gln
                 405                 410                 415

His Leu Phe Met Ile Leu Ala Ser Pro Arg Tyr Val Asp Arg Val Thr
             420                 425                 430

Glu Leu Leu Gln Gln Lys Leu Lys Gln Ser Gln Leu Leu Ala Leu Lys
```

```
                435              440              445
Lys Asp Leu Met Val Glu Lys Gln Gln Glu Ala Leu Gln Glu Gln Ala
    450                 455                 460

Ala Leu Glu Pro Lys Leu Asp Leu Leu Glu Lys Thr Arg Glu Leu
465             470                 475                 480

Gln Lys Leu Ile Glu Ala Asp Ile Ser Lys Arg Tyr Asn Gly Arg Pro
                485                 490                 495

Val Asn Leu Met Gly Thr Ser Val
            500
```

```
<210> SEQ ID NO 7
<211> LENGTH: 28
<212> TYPE: DNA
<213> ORGANISM: Artificial/Unknown
<220> FEATURE:
<221> NAME/KEY: source
<222> LOCATION: (1)..(28)
<223> OTHER INFORMATION: PCR primer

<400> SEQUENCE: 7
cgggatccat ggcacctaaa tcagcttc                                        28

<210> SEQ ID NO 8
<211> LENGTH: 25
<212> TYPE: DNA
<213> ORGANISM: Artificial/Unknown
<220> FEATURE:
<221> NAME/KEY: source
<222> LOCATION: (1)..(25)
<223> OTHER INFORMATION: PCR primer

<400> SEQUENCE: 8
cggaattctc atgagcccgg tctgc                                           25

<210> SEQ ID NO 9
<211> LENGTH: 27
<212> TYPE: DNA
<213> ORGANISM: Artificial/Unknown
<220> FEATURE:
<221> NAME/KEY: source
<222> LOCATION: (1)..(27)
<223> OTHER INFORMATION: PCR primer

<400> SEQUENCE: 9
ccggatccat gcatccttta cagcgtg                                         27

<210> SEQ ID NO 10
<211> LENGTH: 28
<212> TYPE: DNA
<213> ORGANISM: Artificial/Unknown
<220> FEATURE:
<221> NAME/KEY: source
<222> LOCATION: (1)..(28)
<223> OTHER INFORMATION: PCR primer

<400> SEQUENCE: 10
ccgaattctc aggtcaagca attcattg                                        28

<210> SEQ ID NO 11
<211> LENGTH: 5
<212> TYPE: PRT
<213> ORGANISM: Rattus norvegicus
<220> FEATURE:
<221> NAME/KEY: source
<222> LOCATION: (1)..(5)
<223> OTHER INFORMATION: Fragment of library clone
```

-continued

<400> SEQUENCE: 11

Gly Ser Gly Lys Arg
1               5